US005962403A

United States Patent [19]

Kohama et al.

[11] Patent Number: 5,962,403

[45] Date of Patent: Oct. 5, 1999

[54] PERFUME BASE COMPOSITION

[75] Inventors: Makoto Kohama; Junji Koshino, both of Wakayama; Kazuyuki Fukuda; Nao Toi, both of Tokyo, all of Japan

[73] Assignee: Kao Corporation, Tokyo, Japan

[21] Appl. No.: 09/000,146

[22] PCT Filed: Aug. 2, 1996

[86] PCT No.: PCT/JP96/02176

§ 371 Date: Feb. 2, 1998

§ 102(e) Date: Feb. 2, 1998

[87] PCT Pub. No.: WO97/06234

PCT Pub. Date: Feb. 20, 1997

[30] Foreign Application Priority Data

Aug. 4, 1995 [JP] Japan .................................... 7-199637

[51] Int. Cl.[6] .............................. A61K 7/46; C11D 3/50; A61L 9/04

[52] U.S. Cl. ................................ 512/20; 512/3; 510/101; 510/102; 424/76.4

[58] Field of Search .......................... 512/20, 3; 510/102, 510/101; 424/76.4

[56] References Cited

U.S. PATENT DOCUMENTS

| | | | |
|---|---|---|---|
| 4,261,867 | 4/1981 | Fankhauser et al. | 252/522 R |
| 4,267,066 | 5/1981 | Mussinan et al. | 252/174.11 |
| 4,904,465 | 2/1990 | Maillefer | 424/70 |
| 5,336,665 | 8/1994 | Garner-Gray et al. | 512/4 |
| 5,527,768 | 6/1996 | Sprecker et al. | 512/2 |
| 5,531,910 | 7/1996 | Severns et al. | 510/102 |
| 5,554,588 | 9/1996 | Behan et al. | 512/1 |

FOREIGN PATENT DOCUMENTS 0 717 100 6/1996 European Pat. Off. .

OTHER PUBLICATIONS

U.S. Public Health Reports vol. 63, 1948.

Brennan, J.M. Fields Tests With Tick Repellants. U.S. Public Health Reports, vol. 38 (1948), pp. 344 and 346.

Christian Petrier, et al., J. Org. Chem., vol. 50, pp. 5761–5765, "Ultrasound In Organic Synthesis. 7,[1] Preparation of Organic Reagents and Their Nickel–Catalyzed Reactions with α,β–Ultrasound Carbonyl Compounds", 1985.

Pieter S. Van Heerden, et al., Tetrahedron Letters, vol. 33, No. 17, pp. 2383–2386, "Conjugate Addition of Benzyl Copper Reagents to α,β–Enoates and –Enones", 1992.

Koichi Narasaka, et al., Tetrahedron, vol. 48, No. 11, pp. 2059–2068, "Rearrangement of Allylic and Propargylic Alcohols Catalyzed by the Combined Use of Tetrabutylammonium Perrhenate(VII) and p–Toluenesulfonic Acid", 1992.

Giovanni Fronza, et al., Tetrahedron Letters, vol. 36, No. 1, pp. 123–124, "On The Mode of Baker's Yeast Reduction of Benzylidenecyclohexanone", 1995.

J. C. Bardhan, et al., Synthesis of Polycyclic Compounds, Part V, pp. 1809–1813, "Synthesis of Polycyclic Compounds. Part V. The Cyclodehydration of 3–Benzylcyclohexanol", 1955.

*Primary Examiner*—C. H. Kelly

*Assistant Examiner*—Monique T. Cole

*Attorney, Agent, or Firm*—Oblon, Spivak, McClelland, Maier & Neustadt, P.C.

[57] ABSTRACT

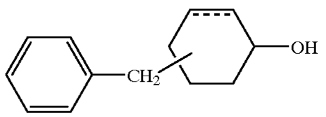

The present invention relates to a perfume base composition comprising a carrier and a benzyl-substituted cyclohexanol having formula (1), wherein the dashed line denotes an optional double bond and the benzyl group is in the 2-, 3- or 4-position of the cyclohexanol ring, with the proviso that the benzyl group is in the 4-position when a double bond is present in the cyclohexanol ring. The composition has not only a well-balanced fragrance but also excellent retentivity of fragrance.

1 Claim, No Drawings

PERFUME BASE COMPOSITION

TECHNICAL FIELD

The present invention relates to a perfume base composition which excellently retains its fragrance. This composition can be used for the production of perfume and other products to be scented such as detergents, cosmetics and sprays.

BACKGROUND ART

A great number of perfume base materials having a floral fragrance have heretofore been known. Among others, aldehyde type perfume bases are the most important perfume base materials. However, since aldehydes are not always stable in fragrant products having different pHs and product forms, these products often do not smell fresh and natural. Moreover, these products do not retain their fragrance for a very long time, which is disadvantageous.

It is accordingly the object of the present invention to provide a perfume base composition which has a floral fragrance and high stability and can impart excellent retentivity of fragrance to blending systems.

DISCLOSURE OF THE INVENTION

This object is achieved by the use of specific benzyl-substituted cyclohexanols, which compounds can impart freshness to the perfume base composition and the products made therefrom. Due to the use of these benzyl-substituted cyclohexanols the articles made from the perfume base composition additionally have a natural, soft and voluminous feeling.

According to the present invention, there is thus provided a perfume base composition comprising a benzyl-substituted cyclohexanol having the following formula (1):

(1)

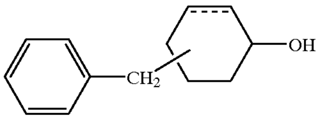

wherein the dashed line denotes an optional double bond and the benzyl group is in the 2-, 3- or 4-position of the cyclohexanol ring, with the proviso that the benzyl group is in the 4-position when a double bond is present in the cyclohexanol ring.

BEST MODE FOR CARRYING OUT THE INVENTION

The benzyl-substituted cyclohexanols (1) are known compounds. For example, 2-benzylcyclohexanol is described in Tetrahedron, 48, 2059 (1992), Tetrahedron Lett., 36, 123 (1994) and J. Chem. Soc., 1809 (1956); 3-benzylcyclohexanol is described in J. Chem. Soc., 1809 (1956); and 4-benzylcyclohexanol and 4-benzyl-2-cyclohexen-1-ol are described in Tetrahedron, 48, 2059 (1992). These documents, however, do not disclose the use of benzylcyclohexanols as a fragrance. Moreover, the prior art does not suggest to use these compounds to retain the fragrance of perfume base compositions and of the products made therefrom.

Examples of the benzyl-substituted cyclohexanols (1) useful in the practice of the present invention include 2-benzylcyclohexanol, 3-benzylcyclohexanol, 4-benzylcyclohexanol and 4-benzyl-2-cyclohexen-1-ol. Of these, 2-benzylcyclohexanol, 3-benzylcyclohexanol and 4-benzylcyclohexanol are preferred with 3-benzylcyclohexanol being particularly preferred.

Cis-trans isomerism exists in the benzyl-substituted cyclohexanols (1) according to the substitution state between the benzyl group and the hydroxyl group on the cyclohexane ring (or cyclohexene ring). In the present invention both cis- and trans-benzylcyclohexanols and mixtures thereof may be used. Among these isomers, the cis-form is particularly preferred.

The benzyl-substituted cyclohexanols (1) can be prepared in accordance with the processes described in the above literature. For example, 2-benzylcyclohexanol (1a) can be prepared by subjecting benzaldehyde (2) and cyclohexanone (3) to aldol condensation and hydrogenating the resulting enone (4) (see the following reaction scheme).

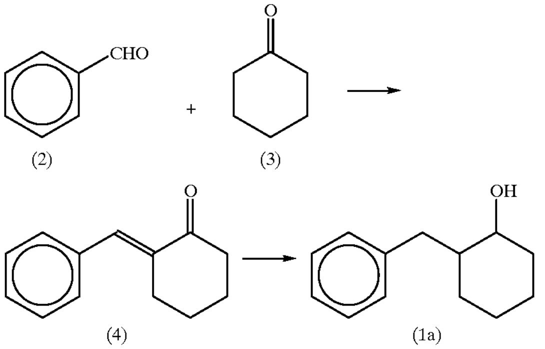

3-Benzylcyclohexanol (1b) can be prepared by subjecting a Grignard reagent (5) prepared from a benzyl halide, and 2-cyclohexen-1-one (6) to 1,4-addition and hydrogenating the resulting ketone (7) (see the following reaction scheme).

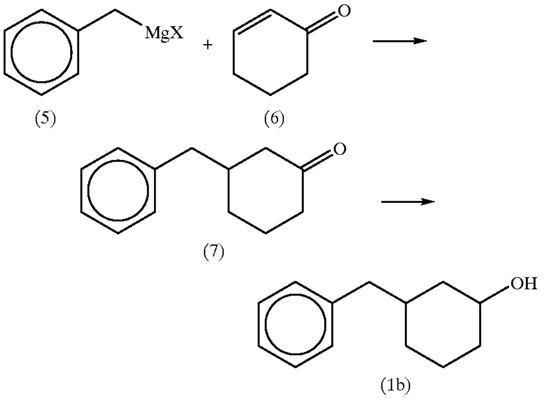

4-Benzylcyclohexanol (1c) and 4-benzyl-2-cyclohexen-1-ol (1d) can be prepared by using an enamine (9) obtained by the dehydration-condensation of 3-phenylpropionaldehyde (8) and morpholine to form 4-benzyl-2-cyclohexen-1-ol (10) by Robinson annellation and selectively hydrogenating only the carbonyl of the compound (10) to form 4-benzyl-2-cyclohexen-1-ol (1d) or hydrogenating both olefin and carbonyl of the compound (10) to form 4-benzylcyclohexanol (1c) (see the following reaction scheme).

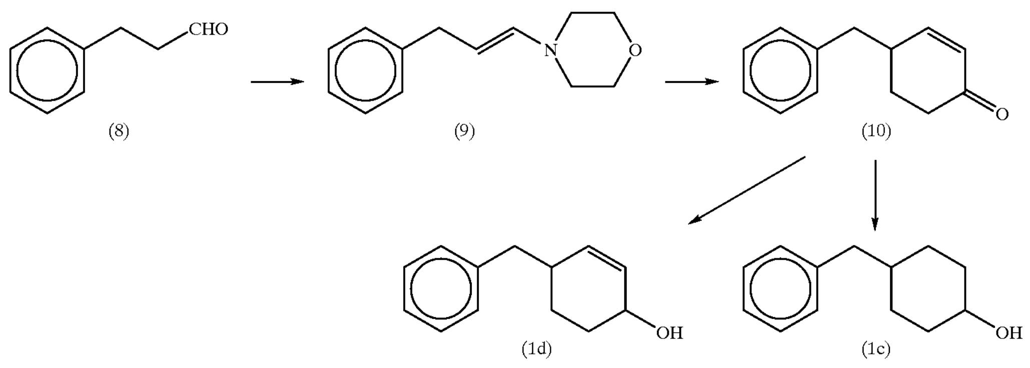

Since most of the benzyl-substituted cyclohexancls (1) obtained in such a manner are mixtures of cis- and trans-forms, their isomers have to be separated from each other by column chromatography, recrvstallization from a hydrocarbon solvent, superfractionation and/or the like if necessary.

The benzyl-substituted cyclohexanols (1) may be used as a deodorant component either singly or in combination with a carrier. Any carrier may be used without any limitation so far as it does not impair the fragrance of the benzyl-substituted cyclohexanols (1). Examples thereof include gaseous, liquid and solid carriers, which may contain other perfume compounds. The examples of the preferable gaseous carriers include a gas for propelland agents. The preferable liquid carriers include water, various organic solvents, and volatile oily substances. The preferable solid carriers include solid oily substances such as various waxes, and polymers. The amount of the benzyl-substituted cyclohexanol (1) to be incorporated in the perfume base composition according to the present invention varies according to the kind of the formulated perfume base used in combination, the kind and intesity of the intended fragrance, and the like, and no particular limitation is imposed on the amount. However, it is generally preferable to use it in a proportion of 0.1–90 wt. %, particularly preferably 0.5–70 wt. % based on the perfume base composition.

In addition to the benzyl-substituted cyclohexanol (1) and the carrier, optional components routinely incorporated in perfume base compositions may be incorporated into the perfume base composition according to the present invention within limits not impeding the effect of the present invention.

The perfume base composition according to the present invention can be obtained by mixing and stirring the benzyl-substituted cyclohexanol (1), carrier and optional components in accordance with a method known per se in the art.

The perfume base composition according to the present invention may be suitably applied to products required to be scented, such as perfumes, detergents, cosmetics, various sprays and fragrances, in particular, toiletry products such as soap, shampoos and rinses.

The perfume base composition according to the present invention has a well-balanced fragrance and is also excellent in retentivity of fragrance.

EXAMPLES

The present invention will hereinafter be described in more detail by the following examples.

Preparation Example 1

A 1-liter four-necked flask equipped with a Dean-Stark trap and a thermometer was charged with 71 g of morpholine and 400 ml of toluene, and 100 g of 3-phenylpropionaldehyde were added dropwise thereto while chilling with ice water, followed by azeotropic dehydration for 1 hour. After cooling the reaction mixture, excess morpholine was distilled off with toluene. The residue was dissolved in 400 ml of toluene. In a 1-liter four-necked flask equipped with a thermometer and a condenser, 70 g of methyl vinyl ketone were added dropwise under reflux to the solution over 1 hour. After aging under reflux for 1 hour, the reaction mixture was cooled, and 10% sulfuric acid was added dropwise to the reaction mixture until the pH of the reaction mixture reached 3. The thus-acidified reaction mixture was then stirred at room temperature for 1.5 hours. After separating the resulting lower water layer, the residual organic layer was neutralized, washed with water, dried and concentrated, thereby obtaining 137 g of a crude product. Dissolved in 500 ml of methanol were 137 g of the crude product, and 4 ml of 4.5 mol/liter aqueous KOH were added dropwise to the solution at room temperature, followed by stirring for 3 hours at the same temperature. After neutralizing the resultant mixture with acetic acid, methanol was distilled off. After the residue was charged into a 1-liter four-necked flask equipped with a Dean-Stark trap and a thermometer to dissolve it in 500 ml of toluene, 2 g of p-toluenesulfonic acid were added to the solution, followed by azeotropic dehydration for 3 hours. After cooling, the residue was neutralized and washed with water, and the resultant organic layer was dried and concentrated, thereby obtaining 119 g of a crude product. This product was purified by column chromatography to obtain 41 g (yield: 30%) of 4-benzyl-2-cyclohexen-1-one.

To a suspension of 3.2 g of lithium aluminum hydride in 500 ml of ether, 30 g of 4-benzyl-2-cyclohexen-1-one were added dropwise at 0° C. After stirring the mixture for 2 hours at the same temperature, it was washed with diluted hydrochloric acid and water, and the resultant organic layer was dried and concentrated, thereby obtaining 31 g of a crude product. This product was purified by column chromatography to obtain 30 g (yield: 98%) of 4-benzyl-2-cyclohexen-1-ol. A ratio of a cis-form to a trans-form was found to be 32:68 by $^{1}$H-NMR.

4-Benzyl-2-cyclohexen-1-ol:

$^{1}$H-NMR δ: 1.17–2.77(8H,m), 4.10–4.30(1H,m), 5.1–5.35(2H,m) 7.1–7.35(5H,m).

Besides, 30 g of the above-obtained 4-benzyl-2-cyclohexen-1-one were hydrogenated at room temperature for 6 hours using 5 g of Raney nickel in methanol under hydrogen pressure (3 kg/cm$^{2}$) until the absorption of hydrogen was stopped. After an organic layer was collected by decantation and concentrated, the residue was purified by column chromatography, thereby obtaining 13 g of cis-4-benzylcyclo-hexanol and 14 g of trans-4-benzylcyclohexanol (yield: 90% in total).

Cis-4-benzylcyclohexanol:

$^1$H-NMR δ: 1.30–1.80(10H,m), 2.54(2H,d,J=6.97 Hz), 3.90–4.01(1H,br), 7.08–7.32(5H,m).

Trans-4-benzylcyclohexanol:

$^1$H-NMR δ: 0.87–1.30(4H,m), 1.35–1.62(1H,m), 1.63–1.85(2H,m), 1.85–2.03(3H,m), 2.47(2H,d,J=7.1 Hz), 3.42–3.62(1H,m), 7.08–7.35(5H,m).

Preparation Example 2

A 500-ml four-necked flask equipped with a thermometer and a condenser was charged with 2.4 g of a piece of magnesium and 120 ml of absolute ether, to which a part of 17 g of benzyl bromide was added with heating. After a reaction started, the remaining amount of benzyl bromide was added dropwise to such a degree that reflux continued. After completion of the drop addition, the resultant mixture was stirred further for 1 hour at room temperature to obtain a liquid reaction mixture. A 500-ml four-necked flask equipped with a thermometer was charged with a suspension of 1 g of copper iodide in 60 ml of absolute ether, to which the liquid reaction mixture was added dropwise at −5° C. After stirring the resultant mixture for 1 hour at the same temperature, it was cooled to −20° C. A solution of 8.6 g of 2-cyclohexen-1-one in 10 ml of absolute ether was added dropwise to the mixture, and the temperature of the resulting liquid reaction mixture was then raised to room temperature while stirring for 24 hours. The liquid reaction mixture was washed with water, dried, filtered and concentrated, and 21 g of the resulting crude product were purified by column chromatography, thereby obtaining 9.6 g (yield: 57%) of 3-benzylcyclohexenone.

Then, 9.6 g of 3-benzylcyclohexenone were hydrogenated at room temperature using 1 g of Raney nickel in methanol under hydrogen pressure (3 kg/cm$^2$) until the absorption of hydrogen was stopped. After an organic layer was collected by decantation and concentrated, the residue was purified by column chromatography, thereby obtaining 4.5 g of cis-3-benzylcyclohexanol and 4.5 g of trans-3-benzylcyclohexanol (yield: 92% in total).

Cis-3-benzylcyclohexanol:

$^1$H-NMR δ: 0.9–1.15(1H,m), 1.17–1.82(8H,m), 1.87–2.15(1H,m), 2.55(2H,d), 7.1–7.4(1H,m), 7.12–7.35 (5H,m).

Trans-3-benzylcyclohexanol:

$^1$H-NMR δ: 0.75–1.35(4H,m), 1.45–1.85(4H,m), 1.85–2.03(2H,m), 2.24–2.62(2H,m), 3.42–3.62(1H,m), 7.08–7.35(5H,m).

Preparation Example 3

A 500-ml four-necked flask equipped with a thermometer was charged with 53 g of benzaldehyde, 25 ml of water and 1 g of sodium hydroxide, to which 68 g of cyclohexanone were added dropwise at 30° C. over 30 minutes. The resultant mixture was stirred for 1 hour at the same temperature. After neutralizing the reaction mixture to separate liquid layers from each other, the resultant reaction product was dissolved in 500 ml of toluene. To the solution, 0.5 g of PTS (p-toluenesulfonic acid) was added to conduct azeotropic dehydration for 3 hours in a 1-liter four-necked flask equipped with a Dean-Stark trap and a thermometer. After cooling, the residue was neutralized and washed with water, and the resultant organic layer was dried and concentrated, thereby obtaining 119 g of a crude product. This product was purified by column chromatography to obtain 24 g (yield: 28%) of 2-benzylidenecyclohexanone.

Then, 10 g of 2-benzylidenecyclohexanone were hydrogenated at room temperature using 1 g of Raney nickel in methanol under hydrogen pressure (3 kg/cm$^2$) until the absorption of hydrogen was stopped. After an organic layer was collected by decantation and concentrated, the residue was purified by column chromatography, thereby obtaining 4.6 g of cis-2-benzylcyclohexanol and 4.4 g of trans-2-benzylcyclohexanol (yield: 88% in total).

Cis-2-benzylcyclohexanol:

$^1$H-NMR δ: 1.1–1.35(1H,m), 1.35–1.85(9H,m), 2.53(1H, dd,J=7.7,13.4 Hz), 2.70(1H,dd,J=9.2,13.3 Hz), 3.75–3.82 (1H,bs), 7.12–7.35(5H,m).

Trans-2-benzylcyclohexanol:

$^1$H-NMR δ: 0.8–1.85(9H,m), 1.91–2.08(1H,m), 2.34(1H, dd,J=9.2,13.3 Hz), 3.17(1H,dd,J=4.0,13.3 Hz), 3.28–3.4 (1H,m), 7.12–7.35(5H,m).

The fragrance of the benzyl-substituted cyclohexanols (1) obtained in the above-described preparation examples are shown in Table 1.

4-benzyl-2-cyclohexen-1-ol, 2-benzyl-cyclohexanol, 3-benzylcyclohexanol and 4-benzylcyclohexanol will hereinafter be referred to as “1d”, “1a”, “1b” and “1c”, respectively. Numerals in ( : ) following each of the symbols indicate the porportions of the cis-form and the trans-form. For example, 1c (0:100) means that the ratio of the cis-form to the trans-form in 4-benzylcyclohexanol is 0:100.

TABLE 1

| Compound | Odor |
|---|---|
| 1d (32:68) | Floral-Green-Muguet Rose-Geranium |
| 1c (100:0) | Floral-Rose-Geranium |
| 1c (0:100) | Floral-Green-Sweet |
| 1b (100:0) | Floral-Grapefruit-Woody-Vetiver |
| 1b (0:100) | Floral-Grapefruit-Vetiver |
| 1a (100:0) | Floral-Grapefruit |
| 1a (0:100) | Floral-Grapefruit |

Example 1

1c (100:0) or the like were added to a rose base having a composition shown in Table 2 and the effect brought about by the addition was evaluated in accordance with an organoleptic test by 5 expert panelists. Organoleptic evaluation standard:

1: The effect of the addition was recognized to a very desirable extent;

2: The effect of the addition was recognized to a desirable extent;

3: The effect of the addition was scarcely recognized;

4: No effect of the addition was recognized, and the balance of fragrance was poor.

TABLE 2

| | Invention product 1 | Comparative product 1 | Comparative product 2 |
|---|---|---|---|
| Rose base: | | | |
| Geraniol | 400 | 400 | 400 |
| Phenylethyl alcohol | 80 | 80 | 80 |
| Geranyl acetate | 80 | 80 | 80 |
| Geranium oil | 50 | 50 | 50 |
| Rhodinol | 50 | 50 | 50 |

TABLE 2-continued

| | Invention product 1 | Comparative product 1 | Comparative product 2 |
|---|---|---|---|
| α-Ionone | 50 | 50 | 50 |
| Diphenyl oxide | 40 | 40 | 40 |
| Linalol | 30 | 30 | 30 |
| 1c (100:0) | 220 | — | — |
| l-Citronellol | — | 220 | — |
| Dipropylene glycol | — | — | 220 |
| Total (parts by weight) | 1000 | 1000 | 1000 |
| Organoleptic evaluation | 1 | 2 | 4 |

The invention product 1 had a voluminous, well-balanced, rose-like fragrance. The comparative product 1 had a rose-like fragrance, but was lacking in a voluminous feeling. The comparative product 2 had an ill-balanced fragrance not associated with roses.

Example 2

A composition having a gorgeous, soft, voluminous, lily of the valley-like fragrance was obtained in accordance with the following formulation.

| (Components) | (parts by weight) |
|---|---|
| Phenylethyl alcohol | 250 |
| Hydroxycitronellal | 250 |
| Bergamot oil | 100 |
| Jasmine oil | 100 |
| Heliotropin | 100 |
| Linalyl benzoate | 50 |
| Phenylethyl acetate | 10 |
| Cinnamic alcohol | 10 |
| 1c (100:0) | 130 |
| Total | 1000 |

Example 3

A floral perfume base for soap, which had a soft, sweet fragrance, was obtained in accordance with the following formulation. In particular, voluminous sweetness was recognized during its use.

| (Components) | (parts by weight) |
|---|---|
| Bois de Rose oil | 250 |
| Terpineol | 150 |
| Lavender oil | 100 |
| Cederwood oil | 100 |
| Citronella oil | 150 |
| Eugenol | 50 |
| Linalyl acetate | 50 |
| Diphenyl oxide | 30 |
| Pearlide BB (product of Kao Corporation) | 70 |
| Styrax resinoid | 20 |
| 1c (0:100) | 80 |
| Total | 1000 |

Example 4

Added to a grapefruit base having a composition shown in Table 3 were 1a (50:50) or 1b (50:50), thereby obtaining grapefruit type perfume base compositions. These compositions were organoleptically evaluated.

TABLE 3

| | Invention product 2 | Invention product 3 |
|---|---|---|
| Grapefruit base: | | |
| Orange oil | 718 | 718 |
| Orange terpeneless oil | 20 | 20 |
| Fruitate*[1] | 20 | 20 |
| Pollenal II*[2] | 20 | 20 |
| Linalol | 10 | 10 |
| Ethyl octanoate | 10 | 10 |
| 2-Methyl-4-propyl-1,3-oxathiane | 2 | 2 |
| 1a (50:50) | 200 | — |
| 1b (50:50) | — | 200 |
| Total (parts by weight) | 1000 | 1000 |

*[1]Kao's specialty chemical; ethyl-bicyclo[5.2.1.$0^{2,6}$]-decane-2-carboxylate.
*[2]Kao's specialty chemical; 2-cyclohexylpropanal.

As a result, the invention product 2 was found to have a grapefruit type natural fragrance with better softness. On the other hand, the invention product 3 was found to have a grapefruit type, natural, fresh, voluminous, and long-lasting fragrance. Of these, the formulated fragrance of the invention product 3, in which 1b (50:50) had been incorporated, was very excellent from the viewpoint of freshness.

Example 5

1a (50:50) or 1b (50:50) were added to a citron base having the composition shown in Table 4 to obtain citron type perfume base compositions. These compositions were organoleptically evaluated.

TABLE 4

| | Invention product 4 | Invention product 5 |
|---|---|---|
| Citron base: | | |
| Orange oil | 298 | 298 |
| Mandarin oil | 150 | 150 |
| γ-Terpinene | 100 | 100 |
| Linalol | 200 | 200 |
| Dihydromyrcenol | 50 | 50 |
| Dimethyloctenone | 50 | 50 |
| Dihydrojasmonate | 50 | 50 |
| 2-Methyl-4-propyl-1,3-oxathiane | 2 | 2 |
| 1a (50:50) | 100 | — |
| 1b (50:50) | — | 100 |
| Total (parts by weight) | 1000 | 1000 |

As a result, the invention product 4 was found to be a citron type natural perfume base composition having better softness. On the other hand, the invention product 5 was found to be a natural, fresh citron type perfume base composition feeling like the rind of a citron. Of these, the formulated fragrance of the invention product 5, in which 1b (50:50) had been incorporated, was very excellent from the viewpoint of freshness.

We claim:

1. A perfume base composition comprising a carrier and 4-benzyl-2-cyclohexen-1-ol.

* * * * *